United States Patent [19]

Anderson

[11] Patent Number: 4,822,735
[45] Date of Patent: Apr. 18, 1989

[54] T CELL GROWTH FACTOR AND METHOD OF MAKING SAME

[75] Inventor: David W. Anderson, Littleton, Colo.

[73] Assignee: Eleanor Roosevelt Institute for Cancer Research, Inc., Denver, Colo.

[21] Appl. No.: 925,188

[22] Filed: Oct. 31, 1986

Related U.S. Application Data

[62] Division of Ser. No. 460,727, Jan. 25, 1983, Pat. No. 4,623,622.

[51] Int. Cl.$^4$ .................. C12P 21/00; C12N 15/00; C12N 5/00; C12R 1/91
[52] U.S. Cl. .................................. 435/68; 435/172.1; 435/240.2; 435/948; 935/101; 935/109
[58] Field of Search .................. 435/68, 172.2, 172.1, 435/240.26, 948; 935/34; 530/351

[56] References Cited

U.S. PATENT DOCUMENTS 4,473,642  9/1984  Gillis .......................... 435/68

OTHER PUBLICATIONS

Stadler et al, Journal of Immunology 127(5) pp. 1936-1940 (1981).
Okada et al, Proc. Natl. Acad. Sci. 78(12) pp. 7717-7721 (1981).
Irigoyen et al, Journal of Experimental Medicine 154 pp. 1827-1837 (1981).
Harwell et al, Journal of Experimental Medicine 152 (4) pp. 893-904 (1980).
Arnold et al, Journal of Immunological Methods 29 pp. 353-360 (1979).
Schrader et al, Journal of Immunology, 126(3) pp. 1101-1105 (1981).
Szybalski et al, Proc. Soc. Exp. Biol. Med. 101 pp. 662-666 (1959).
Littlefield, Science 145 pp. 709-710 (1964).

Primary Examiner—John Edward Tarcza
Attorney, Agent, or Firm—Beveridge, DeGrandi & Weilacher

[57] ABSTRACT

A mutant T-cell line of HSB-2-ERICR which produces a T cell Growth Factor is disclosed. The Mutant cells are sensitive to HAT Medium.

9 Claims, 3 Drawing Sheets

T CELL GROWTH FACTOR AND METHOD OF MAKING SAME

This is a divisional of co-pending application Ser. No. 460,727 filed on Jan. 25, 1983, now U.S. Pat. No. 4,623,622.

The immune system protects the body from a myriad of "foreign" invaders—bacteria, fungi, viruses, and parasites—as well as internal invaders—cancer cells. Two important components of the immune system are B-lymphocytes (antibody producers) and T-lymphocytes. The T-lymphocytes function as regulators and effectors in protecting the body against foreign maladies. T lymphocytes can function as helper cells, killer cells, or suppressor cells. Helper cells cooperate with B lymphocytes for antibody production or with generating other T cell responses. Killer T cells can eliminate virus infected cells and cancer cells or reject foreign grafts. Suppressor T cells serve to shut down responses thus preventing "over reaction". T lymphocytes can function as cells or through the release of soluble factors (cytokines) specifically known as lymphokines. See DeWeck, A. L. "Lymphokines, monokines, and cytokines: an increasingly valuable object for studies in molecular immunology", *Molecular Immunology* 17: 535–537, 1980.

An antigen is a substance which is capable, under appropriate conditions, of inducing a specific immune response and of reacting with the products of that response, that is, with specific antibody or specifically sensitized T-lymphocytes (or their products), or both. Antigens may be soluble substances, such as toxins and foreign proteins or polysaccharides, lipids and nucleic acid, or particulate, such as bacteria and tissue cells; however, only the portion of the foreign molecule known as the antigenic determinant combines with antibody or a specific receptor on a lymphocyte.

An antibody is an immunoglobulin molecule that has a specific amino acid sequence by virtue of which it interacts only with the antigen that induced its synthesis in cells of the lymphoid series (especially plasma cells), or with antigen closely related to it. Antibodies are classified according their biochemistry and to their mode of action as agglutinins, bacteriolysins, hemolysins, opsonins, precipitins, etc.

Cell mediated immunity refers to the specific acquired immunity in which the role of small lymphocytes of thymic origin (T-lymphocytes) is predominant; it is responsible for resistance to infectious diseases caused by certain bacteria, fungi, and viruses, certain aspects of resistance to cancer, delayed hypersensitivity reactions, certain autoimmune diseases, and allograft rejection, and plays a role in certain allergies.

Lymphokines are important mediators of biological responses; not only are immune responses regulated by these molecules but other physiological systems are influenced and affected by them. The study of lymphokines is at present extremely important for a better understanding of regulatory functions in the immune system and other systems in health and disease. The biological characterization of lymphokines is still in its preliminary stages. This is primarily due to the small amount of lymphokines produced in in vitro systems. These substances are active at extremely low physiologic concentrations. Furthermore, when dealing with crude lymphokine preparations there are antagonistic factors, different molecules which have the same biological activity or one molecule having several activities—all of which interfere with bioassays to define specific lymphokine function.

Therefore, there is a need for large-scale lymphokine production in pure form to facilitate the study of these important molecules. The use of cloned leukemic cell lines may provide the link needed for increasing our understanding of the cellular mechanisms of lymphokine production, the interaction of these molecules with target cells, and the isolation and biochemical characterization of individual lymphokines for research and clinical use.

INTRODUCTION TO INVENTION

Leukemic cell lines have provided a wealth of information regarding our understanding of lymphocyte differentiation and maturation. See Minowada, J. "Markers of human leukemia-lymphoma cell lines reflect hematopoietic cell differentiation." *Human Lymphocyte Differentiation: Its Application to Cancer* (eds. B. Serron and C. Rosenfeld, p. 337, North Holland Press, 1978.

These leukemias are lymphocytes "frozen" in a particular stage of cell development and have characteristics of the subpopulation from which they were derived. See Seligmann, M., Preud 'Homme, J. and Brouet, J. "Human Lymphoproliferative diseases as models of lymphocyte differentiation." *Human Lymphocyte Differentiation: Its Application to Cancer*, supra, p. 133. Self-propagating cell lines are therefore a useful source of homogeneous biologically active lymphokines. See Gills, S. and Watson, J. Biochemical and biological characterization of lymphocyte regulatory molecules. V. Identification of an interleukin-2-producing human leukemia T cell line, *J. Exp. Med.* 152: 1709–1719, 1980. Gootenberg, J., Ruscetti, F. and Gallo, R. A biochemical variant of human T cell growth factor produced by a cutaneous T cell lymphoma cell line. *J. Immunol.* 129: 1499–1505, 1982. Sorg, C. and Wolfgang, K. Chemical characterization of products of activated lymphocytes. *Federation Proc.* 37: 2748–2753, 1978. White, R. J. and Klein, F. Large-scale production of human lymphoblastoid interferon. *Cancer Treatment Reviews* 7: 245–252, 1980. Yoshida, T., Kuratsuji, T., Takada, A., Takada, Y. Minowada, J. and Cohen, S. Lymphokine-like factors produced by human lymphoid cell lines with B or T cell surface markers. *J. Immunol.* 117: 548–554, 1976. Stadler, B., Dougherty, S., Farrar, J. and Oppenheim, J. Relationship of cell cycle to recovery of IL 2 activity from human mononuclear cells, human and mouse T cell lines, *J. Immunol.* 127: 1936, 1981.

T-lymphocytes are the source of many lymphokines which play a critical role in controlling immune responses and maintaining human health. See Moretta, L., Mingari, M. C., and Moretta, A. "Human T-cell subpopulations in normal and pathological conditions," *Immunological Rev.* 45: 163–193, 1979. The lymphokine which regulates the T cell's own proliferation and differentiation is extremely important to isolate, purify, characterize, and study at the basic and clinical levels. This important lymphokine is known as T cell growth factor (TCGF) and is sometimes also referred to as interleukin-2 (IL-2); see Grönvik, K. and Andersson, J. "The role of T cell growth stimulating factors in T cell triggering." *Immunological Rev.* 51: 35–59, 1980. Rosenberg, S. A., Schwarz, S., Spiess, P. and Brown, J. "In vitro growth of murine T cells. III. Methods for separation of T cell growth factor (TCGF) from concanavalin A and biological activity of the resulting TCGF." *J. Immunological Methods* 33: 337-350, 1980. Smith, K., Gillis, S., Baker, P., and McKenzie, D. "T-cell growth factor-mediated T-cell proliferation." *Annals N.Y. Academy Sci.* 332: 423-432, 1979. Smith, K., Lachman, L., Oppenheim, J. and Favata, M. "The functional relationship of the interleukins." *J. Exp. Med.* 151: 1551-1556, 1980.

A method has been reported for the long-term culturing of normal human T lymphocytes from peripheral blood or bone marrow, see Morgan, D. A., Ruscetti, F. and Gallo, R. "Selective in vitro growth of T lymphocytes from normal human bone marrows." *Science* 193: 1007-1008, 1979. Success of such cultures depended upon the addition of a growth factor from lectin stimulated normal human peripheral blood lymphocytes. Lectin is a plant extract named according to the species from which it was derived. This factor has been termed T cell growth factor (TCGF) or interleukin 2, and is obligatory for proliferation of T cells in culture. See Smith, K., Gillis, S., Baker, P., and McKenzie, D. "T-cell growth factor-mediated T-cell proliferation." *Annals N.Y. Academy Sci.* 332: 423-432, 1979.

According to a new model of T cell activation, ligands, which are specific foreign substances (i.e. antigens) or nonspecific inducers (i.e. lectins, phorbol esters, or cytokines) which interact with the cell to activate production of TCGF by T-producer cells and deliver a first signal to the T-responder cell. See Smith, K. "T cell growth factor". *Immunological Rev.* 51: 337-357, 1980. Following this sequence of events, TCGF then delivers the second signal required to drive the activated (i.e. T lymphocyte that has reacted with a foreign substance) clones of T-responder cells into proliferation. Thus, the T cell immune response to a foreign invader which culminates in the clonal expansion of a set of cells that can respond to that specific invader and work to eliminate it, is controlled by a T-cell lymphokine—TCGF.

Interest in the regulation and function of antigen-reactive human T lymphocytes has stimulated a need for relatively pure T cell growth factor(s) (TCGF), of which interleukin-2 (IL-2) is the best characterized. IL-2 has been described as a 15,000 MW glycoprotein normally made by T3+ T4+ lymphocytes which stimulates long-term proliferation of antigen-specific T cells, enhances thymocyte mitogenesis, induces cytotoxic T cell reactivity and plaque-forming cell responses in cultures of nude mouse spleen cells, and augments natural killer cell activity in the mouse system.

The discovery disclosed in this application is based on the production of T cell growth factor utilizing a human lymphoblastic leukemia cell line, see Anderson, D. W., Hayward, A. and Jones, C. An acute lymphoblastic leukemia which produces human T cell growth factor. *Immunological Communications* 10: 697-706, 1981 (published Feb. 1, 1982). This cell line was originally isolated by Lazarus et al and identified as HSB-2. See Lazarus, H. Barell, E., Oppenheim, S. and Krishan, A. "Divergent properties of two human lymphocytic cell lines isolated from a single specimen of peripheral blood." *In vitro* 9: 303-310, 1974. The original HSB-2 cell line had a trisomy of one F-group chromosome. From evidence obtained thus far the cloned cell line used for the work described herein differs from the original line HSB-2 in that it has a normal karyotype. The distinguishing element from cytogenetic analysis with regard to the cell line used herein is that there is an extra piece of chromosomal material on the long arm of one number seven chromosome. Because of this distinct difference and the fact that other sublines of HSB-2 do not make TCGF it is evident that this is new cell line. See Frank, M., Watson, J., Mochizuki, D. and Gillis, S. "Biochemical and biologic characterization of lymphocyte regulatory molecules. VIII. Purification of interleukin 2 from a human T cell leukemia." *J. Immunol.* 127: 2361-2365, 1981, See Gillis and Watson, *J. Exp. Med.* Supra. The designation therefore given to the cell line used in the experiments to be described herein is HSB-2-ERICR.

In the course of the development of the invention, six human lymphoblastoid cell lines have been screened for the ability to produce TCGF. It has been found that only the acute lymphoblastic leukemia (ALL) cell line HSB-2-ERICR produces a TCGF when stimulated with a suitable inducer under the conditions utilized and described herein. This cell line HSB-2-ERICR can be used to study the physiology and genetics of TCGF production and the biochemistry of this important immunoregulatory molecule.

This is a representation of the amount of TCGF produced by the HSB-2-ERICR cell line compared to normal lymphocytes, Jurkat (a T cell line known to produce TCGF), and non-producer lines.

Figure 3:
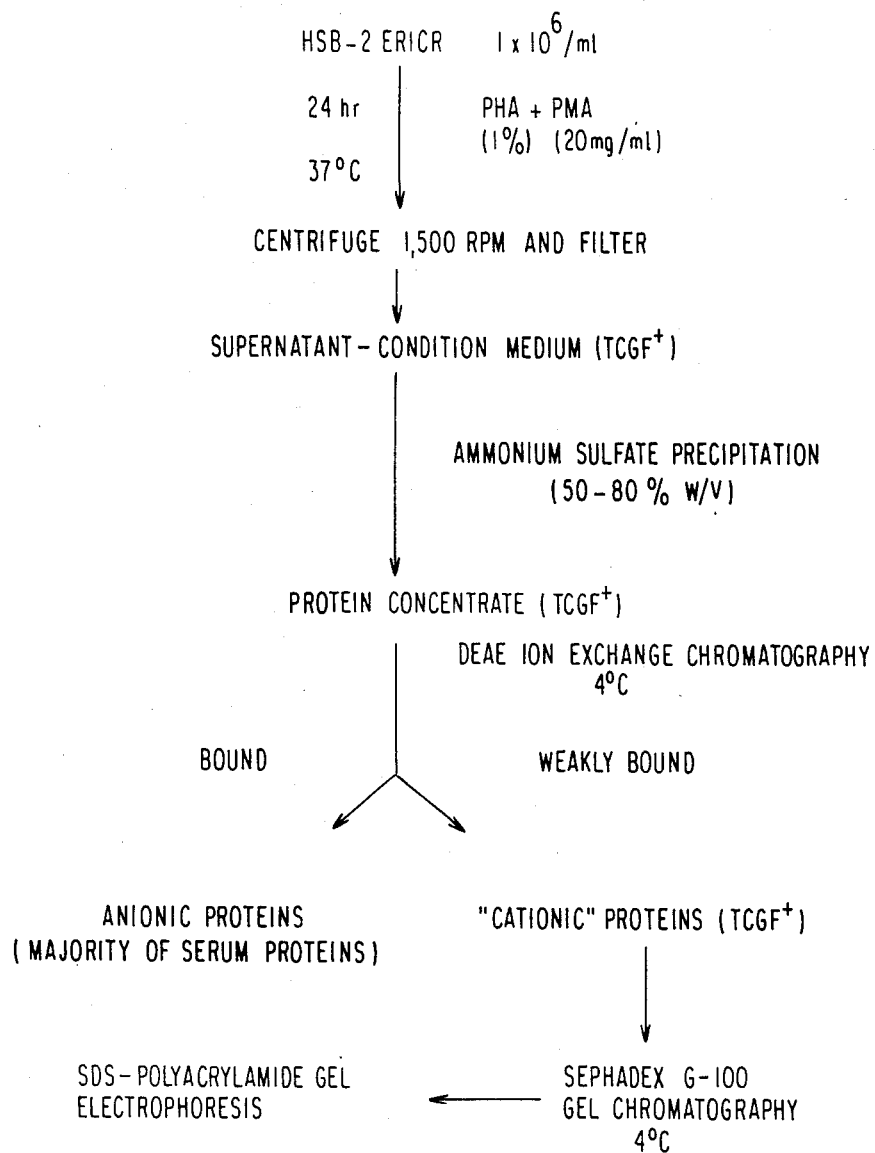

FIG. 3 is a flow diagram showing the overall process of the invention.

DETAILED DESCRIPTION OF INVENTION

Production of TCGF by HSB-2-ERICR

HSB-2-ERICR cells are cultured ($1 \times 10^6$ cells/ml) for 18-24 hr. at 37° C. in RPMI 1640 with 20 mM HEPES in the presence of phytohemagglutinin (PHA; 1% Difco PHA-M, Detroit, MI) and phorbol myristate acetate (20 ng/ml; PMA Sigma, St. Louis, MO). The process can be carried out with PHA alone or along with PMA. Other inducers which activate or stimulate the production of TCGF can be used. For examples lectins, phorbol esters, biological cytokines (including monokines or lymphokines). Fetal calf serum or other sources of serum may be included but is not necessary for TCGF production. That the culture supernatant from stimulated HSB-2-ECICR contains TCGF has been demonstrated by four biological assays: (1) continued proliferation of T lymphocyte PHA-blasts measured by $^3$H-thymidine incorporation; (2) co-stimulator activity for thymocyte division in response to lectin measured by $^3$H-thymidine incorporation into DNA, (3) the ability to support the long-term growth of T cells activated by a specific foreign antigen in culture (growth over four months) and (4) ability to support viability and proliferation of a mouse helper T cell line, HT-2. See Kappler, J., Skidmore, B., White, J. and Marrack, P. Antigen-inducible, H-2-restricted, interleukin-2-producing T cell hybridomas. *J. Exp. Med.* 153: 1198-1214, 1981. All of these activities are attributed to TCGF.

HSB-2 ERICR as a source of TCGF has several advantages over current sources:

(1) rapid growth of cells to high density making large batch preparations possible of growth factor and isolation of nucleic acid for recombinant DNA technology; this eliminates the dependency on clinical specimens which are often difficult to obtain and dependent on availability; HSB-2-ERICR or the HAT sensitive HSB-2-ERICR cell lines as a source of TCGF provide the added advantage over human tissue specimens in that the cultures can be screened and regulated for contaminating viruses or other organisms, thus prevented the need to screen every specimen. Also the problem of collection, transportation and storage associated with human tissue specimens is eliminated;

(2) ability to freeze in liquid nitrogen and recover the cell line for use when needed;

(3) homogeneity of cells and the T-cell growth factor compared to crude preparations made from normal cells;

(4) ability to adapt to new culture conditions for more efficient TCGF production and purification (e.g. serum free cultures or mutant lines for hybridoma production;)

(5) greater activity than produced by equivalent numbers of normal lymphocytes or Jurkat cell line.

(6) near normal karyotype (normal chromosome count with extra material on one number seven chromosome);

(7) stable population with TCGF production from the same clone for over two years;

(8) high yield of activity per cell; and (9) low variability between batches.

HSB-2 ERICR provides a source of TCGF that should greatly facilitate its molecular characterization and the determination of its mode of action and potential therapeutic uses.

CELL LINES

Several in vitro cultured leukemic T and B cell lines were tested for lectin-induced production of T cell growth factor. The cell lines were the following:

CCRF-CEM
MOLT-4
Daudi
HPB-ALL
PBL
Jurkat-FHCRC.

Cells were maintained in RPMI—1640 medium, supplemented with 15% heat-inactivated (56° C. for 30 min.) fetal calf serum (FCS), 100 U/ml penicillin, 100 ug/ml streptomycin, and 20 mM HEPES (referred to as tissue culture medium [TCM]). A variety of TCM can be used for this purpose and are commercially available.

All cell lines tested were obtained from Dr. Allan Epstein, Northwestern University, Chicago, Ill. The cell line Jurkat-FHCRC (obtained from Dr. Philippa Marrack, National Jewish Hospital, Denver, Colo.) reported by Gillis and Watson (see Gillis, S. and Watson, J., *J. Exp. Med.* 152: 1709, 1980) to produce IL-2 was used as a basis of comparison for other possible producer cell lines.

PRODUCTION OF TCGF

Single cell suspensions of mononuclear cells were prepared from fresh surgical specimens of tonsils by pressing the tissue through a 60 mesh wire screen and separating viable cells on Ficoll-Hypaque gradients. These cells were used as controls for TCGF production.

Washed leukemic cells or the control tonsil cells were cultured ($1 \times 10^6$ cells/ml) for 24 hr. in TCM in the presence of phytohemagglutinin (PHA; 1% Difco PHA-M, Detroit, MI) at a temperature of 37° C.

Farrar and Fuller-Bonar (see Farrar, J. J. and Fuller-Bonar, J., Fed. Proc. 39: 802, 1980) and Gillis and Watson, supra, reported that the unsaturated fatty acid derivative phorbol myristate acetate (PMA; Sigma, St. Louis, MO) enhanced TCGF production. In separate experiments, PMA (20 ng/ml) was added to PHA stimulated cultures for TCGF supernatants. After centrifugation to remove cells, the supernatants were collected, filtered through millipore 0.22 $\mu$m filters, and stored at 4° C. or $-20°$ C. until they tested for TCGF activity.

CULTURED T CELLS (CTC)

Continuous cultures of T cells were initiated by stimulating Ficoll-Hypaque-separated peripheral blood lymphocytes (PBL) with PHA as described by Alvarez, et al. See Alvarez, J. M. de Landazuri, M., Bonnard, G. and Herberman, R., *J. Immunol.* 121: 1270, 1978. These cells were maintained in TCM containing 25% TCGF for at least 14 days prior to assay.

TCGF MICROASSAY

The method of Gillis, et al (see Gillis, S. Ferm, M., Ou, W. and Smith K., *J. Immunol.* 120: 2027, 1978) was used to measure TCGF activity of supernatants. Briefly, this method is carried out as follows: CTC were washed and plated in flat bottom microtiter wells ($1 \times 10^5$ cells/well) in RPMI-1640 with 10% FCS. Serial two-fold dilutions of putative TCGF containing supernatants, obtained by the procedures described above, were assayed in duplicate for their ability to stimulate proliferation of CTC during a 48-hr. incubation. The degree of proliferation was measured by incorporation of $^3$H-thymidine (Tdr) added during the last 6 hr. of culture (0.25$\mu$ Ci/well; 5 Ci/mM specific activity, TRA61-Amersham). Cells were harvested on filteres by an automatic cell harvester (Microbiological Associates, Bethesda, Md.) and counted in a scintillation counter.

THYMOCYTE MITOGENIC RESPONSE

The proliferative response of thymocytes to lectins at low cell concentrations ($<1 \times 10^6$/ml) requires exogenous IL-2. See Shaw, J., Monticone, V. and Paetkau, v., J. Immunol. 120: 1967, 1978. TCGF was assayed at 1/16 dilution as described above using fresh thymocytes ($1.5 \times 10^5$ cells at $1 \times 10^6$/ml) in place of CTC lines in 72 hr. microwell cultures with or without 1 ug/ml PHA (Burroughs-Wellcome Company, Greenville, N.C.).

CELL SURFACE CHARACTERISTICS OF HSB-2-ERICR LEUKEMIC CELL LINE

An indirect fluorescent antibody assay as described by Mattes (see Mattes, M., Sharrow, S., Herberman, R. and Holden, H., J. Immunol. 123: 2851, 1979) using OKT monoclonal antibodies (from Dr. Gideon Goldstein, Ortho Laboratories, Raritan, N.J.) determined the phenotype of the TCGF producer, HSB-2-ERICR. Also, sheep red blood cell rosette formation was determined by the method of Lobo, et al. See Lobo, P. Westervelt, F. B. and Horwitz, D., J. Immunol. 114: 116, 1975.

PRODUCTION OF TCGF BY A HUMAN LYMPHOBLASTIC LEUKEMIA CELL LINE

Gillis and Watson have reported on IL-2-producing human leukemia T cell line (Jurkat-FHCRC). It has now been found by applicant that stimulation of HSB-2-ERICR cell line derived from the HSB-2 line (CCRF-HSB-2) originally described by R. A. Adams et al. (Cancer Res. 28: 1121, 1968 Adams, R. et al. The Question of Stem Lines in Human Acute Leukemia Exp. Cell Res. 62, 5, 1970 and distributed through the Sidney Farber Cancer Institute, Harvard Medical School, Boston, MA) by PHA gave a supernatant which contained TCGF activity greater than that obtained from tonsilar or peripheral blood lymphocytes; see FIG. 1.

The other cell lines tested, CCRF-CEM, MOLT-4, Daudi, and HPB-ALL were negative while Jurkat-FHCRC was positive for TCGF production. The addition of PMA to PHA stimulted cultures of HSB-2 ERICR cells augmented the TCGF activity; see FIG. 2. The mechanism of PMA enhancement of TCGF production is not known although a macrophage replacement activity is hypothesized. This finding was unexpected because the HSB-2 ERICR line does not have the cell surface markers associated with TCGF production (i.e. $OKT_3+OKT_4$). See Anderson et al, supra, and Gillis & Watson, JEM 152: 1709, Palacios, R. J. Immunol. 129: 2586, 1982 and Immunol. Rev. 63: 73, 1982.

THYMOCYTE MITOGENIC RESPONSE

Additional evidence that the cell-free supernatants from HSB-2ERICR cells stimulated with PHA and PMA contain TCGF is demonstrated by the co-stimulator activity of these supernatants on thymocytes. This shown in Table I.

DETAILED DESCRIPTION OF DRAWINGS

Figure 1:
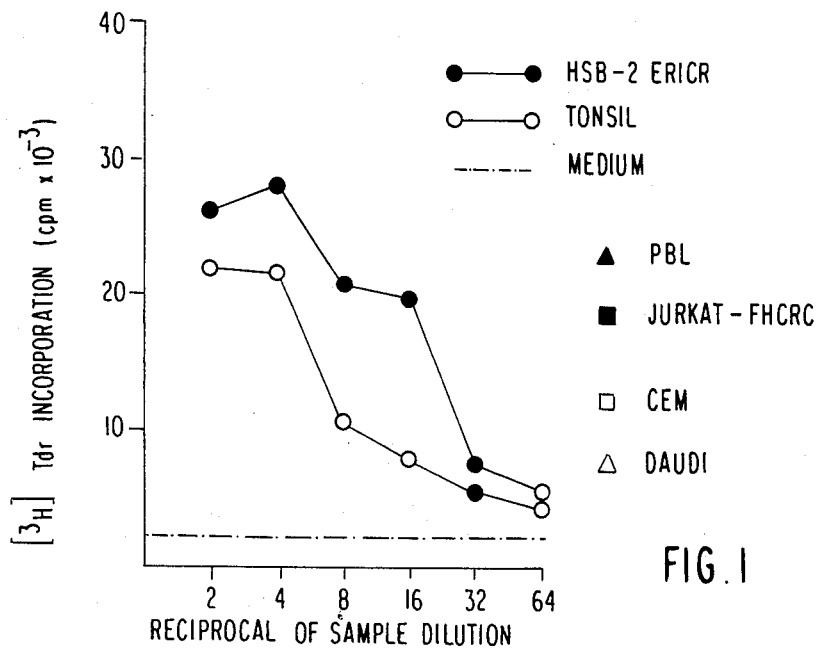
FIG. 1 and FIG. 2 are plots of the Tdr (radioactivity) incorporated as a function of the reciprocal of sample dilution.

In greater detail, FIG. 1 shows the production of TCGF by HSB-2 ERICR and tonsil cells using CTC as responding cells in a quantitative microtiter well assay. Data represents the means of three experiments: - - - HSB-2 ERICR; o- - -o tonsil; .-.-.- medium. The results of supernatants (50% concentration) from several other cell types are included: ( ) PBL; ( ) Jurkat-FHCRC; (□) CEM; (Δ) Daudi. The standard errors of the means were less than 10% of the mean values.

Figure 2:
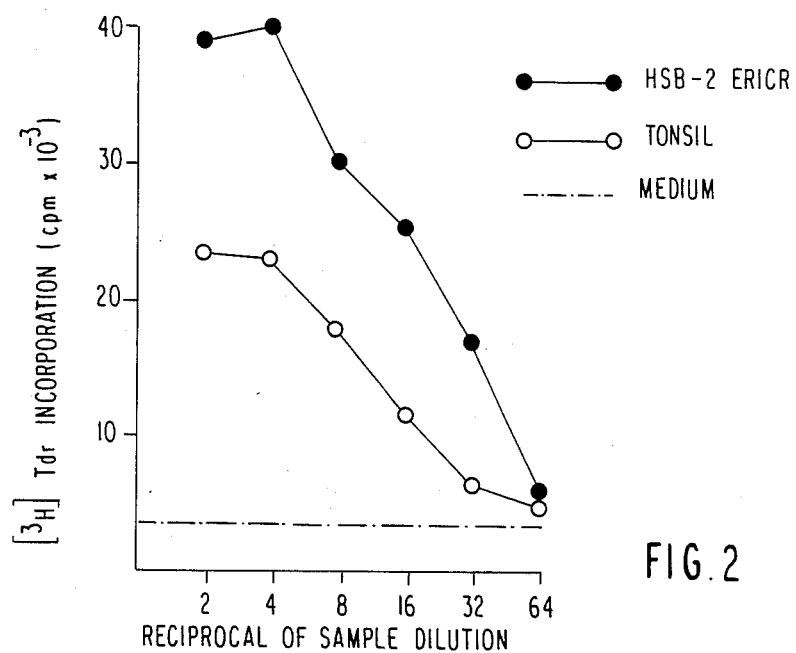

In greater detail, FIG. 2 shows the effect of phorbol myristate acetate (PMA) on TCGF production in PHA stimulated cultures. Supernatants tested on CTC as responding cells in a quantitative microtiter well assay. Data represents the means of three experiments: - - - HSB-2 ERICR: o- - -o tonsil; .-.-.- medium. Standard errors of the means were less than 10% of the mean values.

FIG. 3 shows the overall sequence of steps and especially the protein purification step which is discussed hereinafter.

TABLE I

| Thymocyte Mitogenic Response | | |
|---|---|---|
| Source of TCGF | PHA | Proliferation Index* |
| Control | − | Less than 1 |
|  | + | 1** |
| HSB-2 ERICR | − | 18 |
|  | + | 31 |
| Jurkat | − | not done |
|  | + | 29 |

TABLE I-continued

| Thymocyte Mitogenic Response | | |
|---|---|---|
| Source of TCGF | PHA | Proliferation Index* |
| Tonsil | − | 11 |
|  | + | 20 |

*Proliferation Index = $\frac{\text{Mean cpm Experimental}}{\text{Mean cpm Control + PHA}}$
**Data from 5 experiments. Mean control + PHA = 537 cpm

LONG TERM CULTURES OF ANTIGEN SPECIFIC T CELLS MAINTAINED IN HSB-2 ERICR TCGF

Purified protein derivative (PPD)-specific human T cell lines were established by incubating peripheral blood mononuclear cells with 100 ug PPD/ml in RPMI-1640 with 1.0% autologous human serum for 72 hr. The cells from these cultures were expanded and maintained in Costar flasks in TCM supplemented with 25% TCGF from PHA-PMA stimulated HSB-2 ERICR cells. Three separate cell lines were maintained for over four months by splitting the cultures every five days. That the PPD-specific T cell lines continued to proliferate during their in vitro culture with HSB-2 ERICR growth factor was indicated by their uptake of Tdr when they were tested at day 50. This is reported in Table II. This conclusion was supported by visual inspection of the culture flasks under a phase microscope, although repeated formal cell counts were not performed.

TABLE II

| Stimulation of Antigen Specific T Cells by TCGF | | |
|---|---|---|
| Culture Additive | Normal PBL 3H-Tdr Incorporation (Mean CPM ± SEM) | PPD Specific T Cells 3H-Tdr Incorporation (Mean CPM ± SEM) |
| Medium | 2,515 ± 168 | 3,817 ± 292 |
| HSB-2 ERICR TCGF* | 2,012 ± 214 | 87,020 ± 3,740 |
| Tonsil TCGF* | 3,433 ± 609 | 38,265 ± ,1279 |

Norman human PBL (separated on ficoll-hypaque the day of assay) and PPD-activated PBL, maintained in TCM containing TCGF for 50 days, were cultured in microtiter wells (1 × 10^5 cells/ml) and assayed for a 72 hr. response to TCGF (50%) as described in Materials and Methods. Data represents means of triplicate runs ± standard error of the means.

*TCGF produced as described in Materials and Methods for PHA—PMA stimulation.

CELL SURFACE CHARACTERISTICS OF HSB-2 ERICR LEUKEMIC CELL LINE

The phenotype of HSB-2 ERICR (Table III) is identical to that described for this cell by Reinherz, et al. See Reinherz, E., Kung, P., Goldstein, G., Levey, R. and Schlossman, S., Proc. Natl. Acad. Sci. USA 77: 1588, 1980. Furthermore, only about 30–40% of these cells form rosettes with sheep red cells. Although this cell line is classified as a T cell ALL by Minowada (see Minowada, J., *Human Lymphocyte Differentiation: Its Application to Cancer*, Edited by B. Serron and C. Rosenfeld, p. 337, North Holland Press, 1978) and is positive for terminal deoxynucleotidyl transferase, it does not express sheep erythrocyte receptors or any of the OKT markers specific for T cells. The HSB-2-ERICR and the selected HAT sensitive HSB-2 ERICR cell lines used herein have a normal karotype, that is, normal except for extra chromosomal material on one number 7 chromosome.

TABLE III

Cell-Surface Characteristics of HSB-2 ERICR
Reactivity with Monoclonal Antibodies

| | OKT3 | OKT4 | OKT5 | OKT6 | OKT8 | OKT9 | OKT10 | SRBC Rosette |
|---|---|---|---|---|---|---|---|---|
| HSB-2 ERICR | − | − | − | − | − | + | + | − |
| HSB-2 ERICR Stimulated with PHA | − | − | − | − | − | + | + | − |

*Following PHA stimulation, 95% of the HSB-2 cells were dead as determined by trypan blue uptake. Those cells which survived were cultured and stimulated with PHA. They produced lower quantities of IL-2 (data not shown) but had the same phenotype.

PURIFICATION AND CHARACTERIZATION OF TCGF PRODUCED BY HSB-2 ERICR

PROTEIN PURIFICATION

Protein supernatants from stimulated HSB-2 ERICR cells are concentrated by 50–80% ammonium sulfate precipitation at 4° C. overnight. The precipitate is dissolved in buffer [Tris(10 mM) HCl pH 8.0, 0.1% PEG 6,000, 0.1 mM PMSF] and dialyzed. The sample is added to a DEAE-Sephacel ion exchange column and eluted with Tris buffer (see above) NaCl gradient. TCGF is eluted at pH 8.0 with 0–0.05M NaCl. The biologically active fractions are pooled and lyophilized for concentration and storage. The TCGF can be further purified by gel exclusion chromatography on Sephadex G-100. Purity of various fractions can be determined by polyacrylamide gel electrophoresis (PAGE).

The results of the purification of a large batch of TCGF (900 ml) made in cultures with 15% fetal calf serum are contained in Table IV. It can be seen that TCGF is active at microgram quantities of protein. The purification steps eliminated nearly 99% of the protein from the starting crude supernatant.

TABLE IV
Purification of Human TCGF from HSB-2 ERICR

| Fraction | Protein* mg | Total Activity Units | Yield % | Specific Activity Units/mg | Purification -fold |
|---|---|---|---|---|---|
| Crude TCGF | 6,720 | 1 × 10$^6$ | 100 | 149 | 1 |
| Ammonium Sulfate Precipitate | 1,320 | 820,000 | 82 | 621 | 4 |
| DEAE Ion Exchange | 114 | 614,400 | 61 | 5,389 | 36 |
| SDS-PAGE | 0.002 | 80 | 0.004 | 40,000 | 268 |

*Determined by Lowry Method

In another experiment, from one large batch preparation (1 liter) of serum-free crude supernatant, there was obtained 3.0 mg of TCGF which was approximately an 100 fold protein purification. By utilizing three purification steps (ammonium sulfate precipitation, DEAE Sephacel ion exchange chromatography and Sephadex G-100 gel chromatography), there was obtained 10 ml with a total of 569,600 units of activity [Units represent the reciprocal of the dilution which gives a 50% response-viability or counts of radioactivity incorporated into DNA of dividing cells-multiplied by 10 (cf, see Kappler, J., Skidmore, B., White, J. and Marrack, P. "Antigen-inducible, H-2-restricted, interleukin-2-producing T cell hybridomas." *J. Exp. Med.* 153: 1198–1214, 1981)].

This highly purified substance obtained by the method of the present invention did not contain other lymphokines which generally contaminate crude TCGF (i.e. interferon, B-cell growth factor, T cell replacing factor). Polyacrylamide gel electrophoresis demonstrated 3 proteins (the major bands of 14,000–17,000 with activity), indicating considerable purification from at least 20 bands in crude supernatants. Furthermore, these studies indicate that the TCGF produced by HSB-2 ERICR has two unique properties which make it different from TCGF derived from normal lymphocytes or the Jurkat cell line.

The following characteristics may be mentioned with regard to the TCGF of this invention:

(1) A molecular weight of 45,000 when produced in cultures with serum (determined by Sephadex G-100 gel chromatography). The expected molecular weight can be achieved by reduction of the TCGF supernatant by sodium dodecyl sulfate treatment (1% at 90° C. for 2 min.). This indicates that TCGF from HSB-2 ERICR may be aggregating either with itself or serum proteins. The latter is probably the case because TCGF produced in serum free cultures comes off a G-100 column at about 20,000.

(2) The TCGF elutes from a DEAE-Sephacel ion exchange column with a 0–0.05M NaCl buffer. [Tris (10 mM) HCl pH 8.0; 0.1% polyethylene glycol 6,000 and 0.1 mM PMSF (phenylmethylsulfonyl fluoride)]. This is contrary to the reports in the literature where salt concentrations of 0.05 to 0.2M are necessary (see Frank, M., Watson, J., Mochizuki, D. and Gillis, S. "Biochemical and biologic characterization of lymphocyte regulatory molecules. VIII. Purification of interleukin 2 from a human T cell leukemia." *J. Immunol.* 127: 2361–2365, 1981 and Mier, J. and Gallo, R. G. "The purification and properties of human T cell growth factor." *J. Immunol.* 128: 1122–1127, 1982. This property is the same for serum free cultures as well and is therefore most likely not due to the influence of serum proteins but a different electrostatic property from other TCGFs. These findings indicate that TCGF from HSB-2 ERICR may be a new TCGF or that there may be a family of TCGF molecules having similar biological functions while differing in potency and perhaps other biological functions.

The use of standard protein biochemistry or biological methods will be useful for the purification of sufficient quantities of purified TCGF to allow rapid progress in the chemical and biological characterization and exploration of its clinical potential. Also recombinant DNA and hybridoma (using HAT sensitive HSB-2 ERICR) technologies will also lead to large scale production of TCGF.

Use of other products or by-products (organelles, nucleic acid, enzymes, etc.) of the HSB-2-ERICR or HAT sensitive HSB-2-ERICR for basic research, diagnostic or therapeutic applications are also included within the present invention. An example is the use of the nucleic acid to produce and clone genes which code for T cell growth factor or other important molecules. This process involves recombinant DNA technology or genetic engineering. See Williamson, R. *Genetic Engineering*, pp.2–59 Academic Press, NY 1981 and Okayama, H. and Berg, P. High-efficiency cloning of full length cDNA. *Molecular Celluloar Biology*, 2: 161–170, 1982. The purposes for cloning the genes for T cell growth factor are as follows: (1) to produce from messenger RNA (mRNA) complementary DNA (cDNA) for analyzing the structure, organization and expression of this gene or genes; (2) to identify the chromosome coding for TCGF; (3) to produce a library from stimulated HSB-2-ERICR cells to probe for specific TCGF messenger and perhaps other regulatory lymphokine mRNA; and (4) construction of recombinants (plasmids or cosmids) that can express the cloned cDNA, i.e. T cell growth factor genes, directly in selected expression vehicle such as bacterial, yeast cells or mammalian cells for large scale production of this lymphokine to study and test in vivo as an immune modifier.

The RNA is prepared from stimulated HSB-2-ERICR cell by lysis of the cells with six molar guanidinium thiocyanate and ethanol precipitation of the RNA. The polyadenylated (poly A) messenger RNA is obtained by oligo-(dT)-cellulose affinity chromatography. It has been found that maximal yield of poly A messenger RNA is obtained at 15 hours following stimulation as described in the method section. From $1 \times 10^9$ cells 2,728 micrograms total RNA was obtained with 160 micrograms poly A+ mRNA (5.8% of the total). The poly A mRNA was run on a 1% agarose gel in an electrical field (70 volts for 6 hr). Ethidium bromide stained gels indicate that the total poly A mRNA pool contains mRNA of approximately 11S which is the size needed to code for a TCGF molecule of approximately 15,000 daltons. The poly A mRNA will be used in the cDNA gene cloning applying a variety of methods available today. Williams, supra. Okayama & Berg, supra. and Ish-Horowicz, D. and Berk, J. Rapid and efficient cosmid cloning. *Nucleic Acid Res.*, 9: 2989, 1981.

The future of this research with the use of purified TCGF and cloned genes gives much promise. It will be possible with purified TCGF to study growth factor-receptor interaction and the biochemical events induced by this interaction. This will possibly lead to the elucidation of the defects in leukemic cells which allow them to grow independent of TCGF. The cloned genes will not only provide the information and capability outlined above but will also allow one to begin to study at the molecular level gene disfunction (mutation, deletion, aberrant synthesis) of genes controlling growth and differentiation which may be related to the cause of human leukemia. Furthermore, the recombinant DNA and genetic engineering will allow a large scale production of the T cell growth factor produced by this novel and unique cell line.

Potential research and medical applications for TCGF are already evident. TCGF will be useful to grow up (i.e. clone) large quantities of functional T lymphocytes in the laboratory. This will allow scientists to study the mechanisms by which T lymphocytes "see" foreign molecules, how they kill viruses or cancer cells, and the genes and products (lymphokines) which regulate these activities.

Cloned T-cell lines will be useful as tissue typing reagents and may have application in specific therapy for certain infectious agents and tumors. See Paul, W., Sredni, B., and Schwartz, R. "Long-term growth and cloning of non-transformed lymphocytes." *Nature* 294: 697–699, 1981.

The use of TCGF as an immunotherapeutic or immunoenhancing drug has some very promising prospects. Nude mice (athymic), analogous to some human immunodeficiencies, can have their T cell immune response restored with exogenously supplied TCGF. See Smith, K., Gillis, S., Baker, P., and McKenzie, D. T-cell growth factor-mediated T-cell proliferation. *Annals N.Y. Academy Sci.* 332: 423–432, 1979 and Smith, K., Baker, P., Gillis, S. and Ruscetti, F. Functional and molecular characteristics of T cell growth factor. *Molecular Immunology* 17: 579–589, 1980. TCGF deficiency has also been associated with some autoimmune responses and aging in mice (see Dauphinée, M., Kipper, S., Wofsy, D. and Talal, N. "Interleukin 2 deficiency is a common feature of autoimmune mice." *J. Immunol.* 127: 2483–2487, 1981 and Thoman, M. and Weigle, W. "Cell-mediated immunity in aged mice: An underlying lesion in IL-2 synthesis." *J. Immunol.* 128: 2358–2361, 1982) in mice.

Furthermore, TCGF is important in generating natural killer cells (non-T, non-B lymphocytes) which are thought to be very important as a first line defense against cancer cells. See Henney, C., Kuribayashi, K., Kern, D. and Gillis, S. "Interleukin-2 augments natural killer cell activity." *Nature* 291: 335–338, 1981. Warner and Dennert demonstrated that natural killer cells (NK cells) cultured in TCGF could be injected into mice ($2 \times 10^6$ NK cells/mouse) and protect them from melanoma and radiation-induced thymic leukemia. See Warner, J. F. and Dennert, G. Effects of a cloned line with NK activity on bone marrow transplants, tumor development and metastasis in vivo, *Nature* 300: 31–34, 1982.

It has also been demonstrated that cytotoxic T-cells specific for leukemic cells could be cultured in TCGF and then injected into mice to protect them from leukemia. See Smith, K. A., Gillis, S. and Baker, P. E. The inhibition of in vivo tumor growth by cytotoxic T cell lines. *Proc. Am. Ass. Cancer Res.* 20: 93, 1979. It is possible that continuous cultures of human killer T cells cytotoxic for a patients tumor cells could be expanded in vitro and used for immunotherapeutic treatment of cancer patients. Exogenously supplied TCGF may be used to activate natural killer or cytotoxic T lymphocytes in the body and thus help combat cancer. Hefeneider et al See *J. Immunol* 130: 222–227; 1983 have demonstrated that mice treated with TCGF (IL-2) generate more cytotoxic T cells specific for the cells of an accompanying tumor challenge. Also mice injected with TCGF (IL-2 50–100 Units) intraperitoneally generate more natural killer cells than control mice.

Finally, it has been demonstrated that TCGF can control interferon production. See Farrar, W., Johnson, H. and Garrar, J. "Regulation of the production of immune interferon and cytotoxic T lymphocytes by interleukin 2." *J. Immunol.* 126: 1120–1125, 1981 and Torres, B., Farrar, W. and Johnson, H. "Interleukin 2 regulates immune interferon production by normal and suppressor cell cultures." *J. Immunol.* 128: 2217–2219, 1982. Interferon is a lymphokine which regulates suppressor T cells and macrophages, combats viral infections and has antitumor cell activity in vitro and in vivo. Therefore, TCGF has enormous potential as a therapeutic agent in fighting cancer, as an adjuvant in vaccines for stimulating the immune system, as an inducer of interferon, and to augment or modulate defective immune systems in immunodeficiencies (agammaglobulinemia, acquired immunodeficiency syndrome, athymic conditions), in autoimmunities (rheumatorid arthritis, systemic lupus erythematosus, etc.), and in the aged.

The TCGF produced in accordance with this invention can be utilized in the form of a therapeutic compoisiton when admixed with a liquid pharmaceutically acceptable nontoxic carrier. Such pharmaceutical carriers can be steril liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerole solutions can also be employed as liquid carriers, particularly for injectable solutions. Suitable pharmaceutical carriers are described in "Remington's Pharmaceutical Sciences" by E. W. Martin. Such compositions will contain an effective therapeutic amount of TCGF together with a suitable amount of carrier so as to provide the form for proper administration to the host.

The foregoing description illustrates the capacity of HSB-2 ERICR lymphoblastic leukemia to produce a human T cell growth factor. HSB-2-ERICR derived TCGF has the ability to sustain in vitro proliferative activity of continuous T cell PHA-induced blasts as is shown in FIGS. 1 and 2, act as a co-stimulator for thymic cells (Table I), and suport the long-term culture of antigen specific T cell blasts (Table II).

HSB-2 cells were previously tested for IL-2 or TCGF production by Gillis and Watson, supra, and found negative. Differences in assay conditions are unlikely to be important as the assay methods used therein are similar to those described by Gillis, et al, supra. Nevertheless the activity in HSB-2 ERICR supernatants has been referred to for purposes of this invention as "TCGF" rather than "IL-2" because it is the "TCGF" activity which is observed. Significant differences are already apparent.

The TCGF produced by the present invention has two unique properties:

(1) A molecular weight of 45,000 when produced in cultures with 10% FCS (determined by Sephadex G-100 gel chromatography). The expected molecular weight of 15,000–20,000 is achieved by reduction with sodium dodecyl sulfate (1%, 90° C. for 2 min). TCGF from HSB-2 ERICR may be aggregating either with itself or serum proteins. The latter is probably the case since TCGF from serum free cultures comes off a G-100 column at about 20,000 daltons, (2) TCGF elutes from a DEAE-Sephacel column with low salt buffer. This indicates a cationic nature which is contrary to reports in the literature (Frank et al, J. Immunol. 127: 2381, 1981; Mier and Gallo, J. Immunol. .28: 1122, 1982). This property is the same for serum free cultures as well and is therefore most likely due to the molecular nature of this TCGF and not serum proteins. Highly purified TCGF is unstable although stability is enhanced and maintained by: (1) addition of 0.1% PEG 6,000; (2) addition of proteins such as bovine serum albumin; (3) addition of an antiproteolytic agent PMSF; and (4) lyophilization and storage at −70° C. When run on SDS-PAGE (7% acrylamide) HSB-2 ERICR TCGF yields a major band with acitivity (14,000–15,000 daltons) and several minor bands. The activity of these bands and the relationship to each other has not been determined. It has been concluded that HSB-2 ERICR TCGF is a unique variant form of this lymphokine. These findings indicate that TCGF in general may consist of a family of biochemically different molecules with shared and unique biologic acitivity.

HSB-2 ERICR cells used in the present invention lack the phenotype of mature T cells in that they are negative for surface T3+, 4+, 6+, 8+ as were the HSB-2 cells studied by Reinherz, et al, supra, so there is no phenotypic evidence for heterogeneity in HSB-2 ERICR.

The production of TCGF by the HSB-2 ERICR cells as described herein is of particular interest in view of their lack of the T3+ and T4+ antigens previously associated with TCGF production. Jurkat cells, in contrast, are T3+ and so are more closely related to mature blood T cells. Neverthless, HSB-2 ERICR cells used herein produced TCGF activity equal to or better than Jurkat-FHCRC in numerous experiments.

Preliminary studies show that the TCGF made by the PHA-PMA stimulated HSB-2 ERICR cells used herein eluted from Sephadex G-100 in the same position as the 45,000 MW ovalbumin marker. The difference in size, which is three times that IL-2 made by human blood lymphocytes, seems too large to be due to differences in glycosylation or sialylation. The TCGF produced by HSB-2 ERICR cells may have a different conformation due to altered secondary structure or perhaps because of aggregation with itself or with other macromolecules, thus giving it an apparent molecular weight of 45,000. This seems to be the case with mouse IL-2 isolated from cell culture which appears to be a dimer. See Caplan, B., Gibbs, C. and Paetkau, V., J. Immunol. 126: 1351, 1981. However, the relationship between TCGF produced by HSB-2 ERICR and IL-2 and perhaps other T cell growth factors remains to be determined.

Since T-ALL's are thought to be derived from immature thymocytes, leukemia cell lines can be related to different proposed stages of intrathymic differentiation utilizing the monoclonal antibody series developed by Reinherz, et al, supra. An investigation of the diversity of various lymphocyte subpopulations and leukemia cell lines which produce TCGF or IL-2 will help determine the phenotype(s) of the TCGF producer(s) and help define the ontogeny of T cells with this function.

Studies of a continuous T cell leukemic line with the capacity to produce IL-2 or a TCGF may provide additional understanding of normal IL-2 production (mechanism of triggering of IL-2 release and regulatory control mechanisms) as well as provide a source of high quaity TCGF for biochemical and physiological studies.

The TCGF produced in accordance with the present invention may be used for many purposes, as for example, in treatment of athymic (immunodeficient) warm blooded mammals. Illustratively, treatment of athymic nude mice with a dose of TCGF administered subcutaneously gave the following results:

Nude mice, which do not contain detectable levels of immunocompetent T cells, cannot generate cytotoxic or killer T cells to allogeneic (foreign) cells. See Kindred, B. "Nude Mice in Immunology". Prog. Allergy, Vo. 26, 137, 1979. Wagner et al (T Cell Derived Helper Factor Allows In Vivo Induction of Cytotoxic T Cells in nu/nu Mice., Nature 284, 278, 1980) demonstrated that nude mice given allogeneic stimulator cells plus partially purified IL-2 were able to generate cytotoxic T cells. Mice were injected with foreign cells (inactivated with radiation 2,000 rad) subcutaneously on day 0 and injected in the same site as the cells twice a day from day 0 until day 3 with 100 µl of semi-purified IL-2 (T helper factor). In separate experiments, mice received the same treatment; however, administration of the cells and IL-2 were intravenously. On day 5, the lymphocytes from spleens were harvested from the mice and tested for killer cell activity. It was found that nude mice treated by the above procuedures had significant numbers of cytotoxic T cells specific for the genetic strain of the stimulator foreign cells. This demonstrates the ability of IL-2 to modulate and restore a deficient immune system in vivo.

Also, it may be used to aid in the proliferation of normal lymphocytes are reported by Smith: T-Cell Growth Factor, *Immunological Review* (1980), Vol. 51, pages 337 et seq.

A HSB-2 ERICR cell line resistant to 6-thioguanine (20 ug/ml) has been selected and cloned which is HAT (hypoxanthine, aminopterin, thymidine) sensitive and still has the capacity to produce TCGF when stimulated with PHA and PMA (33,434±6,142 cpm; mean of two experiments run at 50% TCGF on continuous lines of PHA T cell blasts). This cell line is useful for the development of somatic cell hybrids which can be employed for (1) large scale production of TCGF by stimulation with inducers which activate the production of TCGF; and (2) studies on genetic control of human TCGF production and the communication network involved in lymphocyte regulation. This information increases insight into the role that aberrant TCGF regulation might play in the etiology of human leukemia and immunologic dyscrasias.

This selected line, unlike the original parent HSB-2 line (established by Lazarus, H., et al.; received from the Sidney farber Cancer Institute, Harvard Medical School, Boston, Mass.), can produce T cell growth factor when stimulated by lectin and PMA.

The HAT sensitive cell line HSB-2-ERICR was selected by growth of the parent line in 20 ug/ml 6-thioguanine (although other selective agents such as 8-azaguinine could be used) and subsequent cloning and expansion of resistant cells in tissue culture medium containing 6-thioguanine. The HAT sensitive HSB-2-ERICR line has a modal chromosome count of 46 with an extra segment on one number seven and like its parent, grows rapidly to a high cell density and thus can be used for large-scale production of TCGF. More importantly, this cell line will be useful for making hybrid cell lines. Such hybrids can be employed in studies to elucidate the chromosome involved in the control and production and perhaps also mechanisms of regulation of TCGF.

This invention was supported by grants from the National Cancer Institute (Ca 18734) and the National Institute on Child Health and Human Development (HD 02080). The HSB-2 ERICR and HAT sensitive HSB-2 ERICR cell lines were deposited on Jan. 21, 1983 at the American Type Culture Collection Depository, 12301 Parklawn Drive, Rockville, Md. 20852 and identified by the deposit numbers CRL 8198 and CRL 8197, respectively.

I claim:

1. A process for preparing T cell growth factor comprising:
   (a) selecting an HAT sensitive strain of HSB-2-ERICR obtained by the process of treating a cell line identified as HSB-2-ERICR with an agent to deactivate the enzyme HGPRT, recovering and choosing cells resistant to said agent and determining sensitivity to HAT medium;
   (b) culturing the cell line in a tissue culture medium;
   (c) contacting the cells so obtained with an inducer which activates or stimulates the production of T cell growth factor;
   (d) recovering the supernatant therefrom.

2. The proces of claim 1 which further includes the steps of testing the biological activity of the supernatant.

3. The process of claim 1 wherein the inducer is a lectin.

4. The process of claim 1 wherein the inducer is a phorbol ester.

5. The process of claim 1 wherein the inducer is a biological cytokine.

6. The process of claim 1 wherein the inducer is a lymphokine or monokine.

7. The process of claim 1 wherein the inducer is PHA or a mixture of PHA and PMA.

8. The process of claim 1 wherein the TCGF is purified from the supernatant.

9. HAT-sensitive HSB-2 ERICR.

* * * * *